United States Patent
Agafontsev (10) Patent No.: US 9,433,481 B2
(45) Date of Patent: Sep. 6, 2016

(54) IMPLANTABLE REPLICA OF NATURAL TOOTH

(71) Applicant: Sergei Anatolievitch Agafontsev, Vancouver (CA)

(72) Inventor: Sergei Anatolievitch Agafontsev, Vancouver (CA)

(*) Notice: Subject to any disclaimer, the term of this patent is extended or adjusted under 35 U.S.C. 154(b) by 10 days.

(21) Appl. No.: 13/914,369

(22) Filed: Jun. 10, 2013

(65) Prior Publication Data

US 2014/0363791 A1    Dec. 11, 2014

(51) Int. Cl.
*A61C 8/00* (2006.01)
*B05D 7/00* (2006.01)
*A61C 13/09* (2006.01)

(52) U.S. Cl.
CPC .......... *A61C 8/0013* (2013.01); *A61C 8/0036* (2013.01); *A61C 13/09* (2013.01); *B05D 7/00* (2013.01)

(58) Field of Classification Search
CPC ...... A61C 8/00; A61C 13/12; A61C 13/225; A61C 13/00; A61C 13/20; A61L 27/30; B05D 7/00
USPC ........................................................ 427/2.24
See application file for complete search history.

(56) References Cited

U.S. PATENT DOCUMENTS

| | | | |
|---|---|---|---|
| 4,536,158 A | 8/1985 | Bruins et al. | |
| 4,878,914 A | 11/1989 | Miwa et al. | |
| 5,004,422 A | 4/1991 | Propper | |
| 5,219,287 A | 6/1993 | Nishihara | |
| 7,708,557 B2 | 5/2010 | Rubbert | |
| 2003/0124490 A1* | 7/2003 | Nielsen | 433/180 |
| 2005/0048440 A1 | 3/2005 | Feng | |
| 2005/0106534 A1* | 5/2005 | Gahlert | 433/173 |
| 2006/0154203 A1 | 7/2006 | Emanuelli | |
| 2007/0116734 A1 | 5/2007 | Akash | |
| 2007/0173952 A1 | 7/2007 | Hermansson et al. | |
| 2007/0264612 A1 | 11/2007 | Mount | |
| 2008/0254201 A1* | 10/2008 | Carinci et al. | 427/2.27 |
| 2009/0092944 A1 | 4/2009 | Pirker | |
| 2011/0003083 A1 | 1/2011 | Yang et al. | |

FOREIGN PATENT DOCUMENTS

| | | |
|---|---|---|
| WO | 9834561 | 8/1998 |
| WO | 2006084346 | 8/2006 |

* cited by examiner

*Primary Examiner* — Dah-Wei D Yuan
*Assistant Examiner* — Andrew Bowman
(74) *Attorney, Agent, or Firm* — Richard D. Okimaw (57) ABSTRACT

A tooth implant comprises a tooth body sized to correspond to a tooth to be replaced and a layer of microscopic protrusions on an outer surface thereof. A method for preparing a dental implant comprising obtaining an model of the tooth to be replaced forming a tooth body corresponding to the model. The method further comprises applying a plurality of particles to at least a root portion of the tooth body and exposing the at least a root portion of the tooth body to a liquid ceramic so as to deposit a layer of cured liquid ceramic material on the at least a root portion of the tooth body.

6 Claims, 8 Drawing Sheets

IMPLANTABLE REPLICA OF NATURAL TOOTH

BACKGROUND OF THE INVENTION

1. Field of Invention

The present invention relates to dentistry in general and in particular to a method and apparatus for providing a replica tooth.

2. Description of Related Art

Teeth play a very important role in good mastification or chewing of food as well as subsequent digestion and appearance for people. Good color, anatomy and healthy well positioned teeth greatly contribute to overall image of the individual. Occasionally, human teeth may lose their integrity or a good appearance due to a variety of reasons to a point where it cannot be restored by means of filling, buildups or crowns. Other times, the tooth may become infected or loos proper bone support.

When such teeth have been removed, a few conventional methods exist to replace such missing teeth, including replacing it with a removable appliance such as a plastic denture or metal frame denture, replace it with a traditional fixed denture or replacement with endosseous implant systems. However such conventional methods have not been satisfactory. In particular, replacement with dentures often requires preparation of the neighboring teeth by grinding and the bridge cemetation may itself be harmful to the adjacent teeth as well as blocking the flow of liquids or air between the teeth.

In the case of dental implants, such implants are commonly formed of at least two components. First a post having a screw or other fastener thereon is inserted into a socket which is drilled and tapped into the bone of the patient. Thereafter a cap is secured to the screw to provide the appearance of a tooth. Such conventional implants require extensive and highly invasive surgical procedures to prepare and place the screw type implant directly into the bone of the patient.

There are currently several difficulties with conventional tooth implants. Such implants are difficult to correspond to the natural tooth anatomy, shape and size and may frequently have a different color, shade, translucency and structure than the natural tooth. The interface of the implant and the gum tissue is not self-cleaning and may be vulnerable to bacterial plaque retention and subsequent inflammation and development of perimplantitis similar to periodontal disease. Additionally, as the implant is directly screwed into the bone of the patient as opposed to interfacing with the gums, such implants do not replicate the natural cosmetics and functions of a tooth within the gum sockets. Due to the direct connection between the implant and the bone, all forces on the tooth are transmitted directly to the bone with no place or ability to have periodontal membranes around the tooth as in natural teeth. It is well known that such periodontal membranes provide a shock absorbing quality to forces on the teeth. Conventional implants may also be difficult to install due to the need to drill and tap holes in the patient's bone to an exact size of standardized implants. It will also be appreciated that the connection between the implant and the bone is difficult to seal thereby potentially harboring more plaque and bacteria. Natural appearing position and alignment may also be difficult with conventional implants.

SUMMARY OF THE INVENTION

According to a first embodiment of the present invention there is disclosed a tooth implant comprising a tooth body having a crown portion and a root portion sized to correspond to a tooth to be replaced and a layer of microscopic protrusions on an outer surface of the root portion.

The tooth body may be formed of an inner core having an outer shell surrounding the crown portion. The inner core may be formed of a material selected from the group consisting of zirconium dioxide and aluminum oxide. The outer shell may be formed of a material selected from the group consisting of zirconium dioxide, aluminum oxide and lithium silicate. The outer shell may be substantially translucent.

Each of the microscopic protrusions comprise microfibers of chains of hydrated minerals. The hydrated minerals may be selected from the group consisting of hydrated alumina, hydrated silica, hydrated titania, hydrated zirconia, hydrated phosphorica and combinations thereof. The microfibers may extend from a later of particles secured to the outer surface of the root portion. The particles may have a size of between 0.05 and 0.2 mm.

According to a further embodiment of the present invention there is disclosed a method for preparing a dental implant comprising obtaining an model of the tooth to be replaced, forming a tooth body corresponding to the model, applying a plurality of particles to at least a root portion of the tooth body and forming a layer of microfibers of chains of hydrated minerals to extend from the plurality of particles.

The tooth body may be formed of a sintered ceramic having a first sintering temperature. The particles may be adhered to the tooth body by sintering. The particles may have a second sintering temperature less than the first sintering temperature.

The microfibers may be formed by applying a layer of liquefied ceramic suspension over the tooth body and plurality of particles heating the dental implant at a temperature less than the second sintering temperature, cooling the dental implant, exposing the dental implant to a solution of sulfuric acid and exposing the dental implant to a solution of phosphoric acid.

The liquefied ceramic suspension comprises a low fusing ceramic material fused with a layer of a flux material mixed in an aqueous base. The ceramic materials may be selected from the group consisting of zirconium dioxide, aluminum oxide and lithium silicate. The flux material may be selected form the group consisting of $Na_2CO_3$, $NaOH$, $K_2CO_3$, $KOH$, $Li_2CO_3$ and $LiOH$. The liquid ceramic material and the flux may be mixed in a ratio of between 15 and 23% ceramic materials. The liquefied ceramic suspension may be prepared by fusing the ceramic materials and the flux materials, cooled, milled to a powder and mixed into an aqueous base.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

In drawings which illustrate embodiments of the invention wherein similar characters of reference denote corresponding parts in each view.

DETAILED DESCRIPTION

Figure 1:
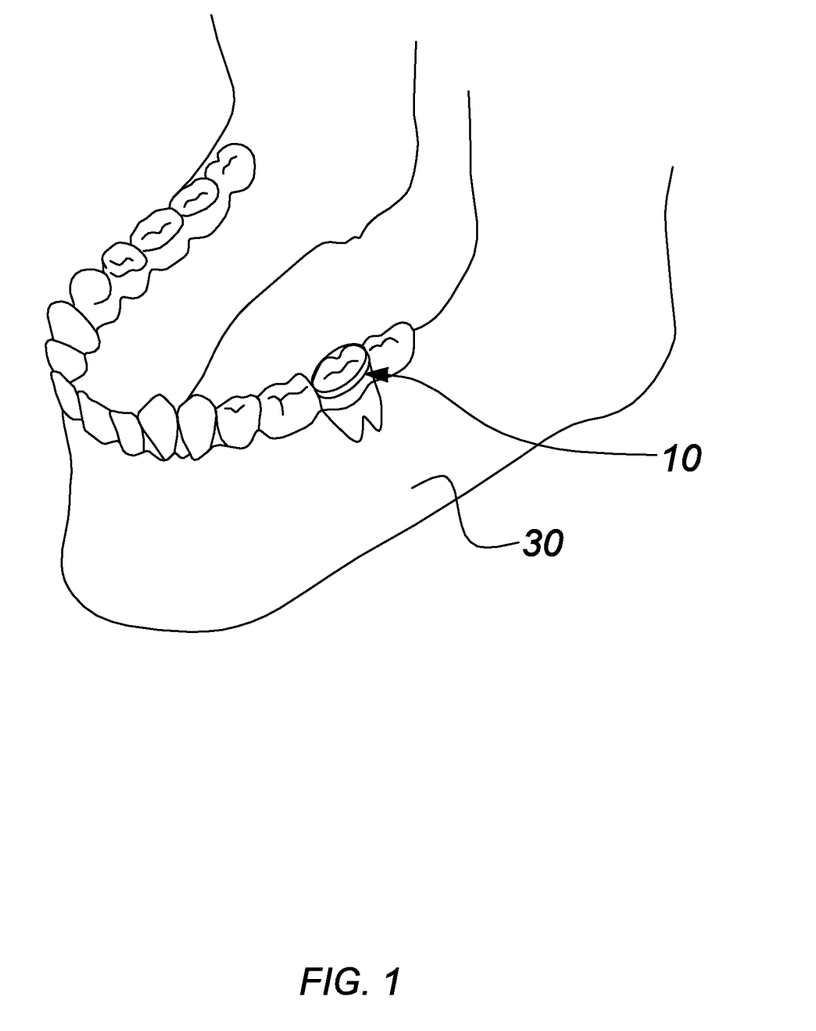
FIG. 1 is a perspective view of a patient's lower jaw having a tooth implant according to a first embodiment of the present invention therein.
Figure 2:
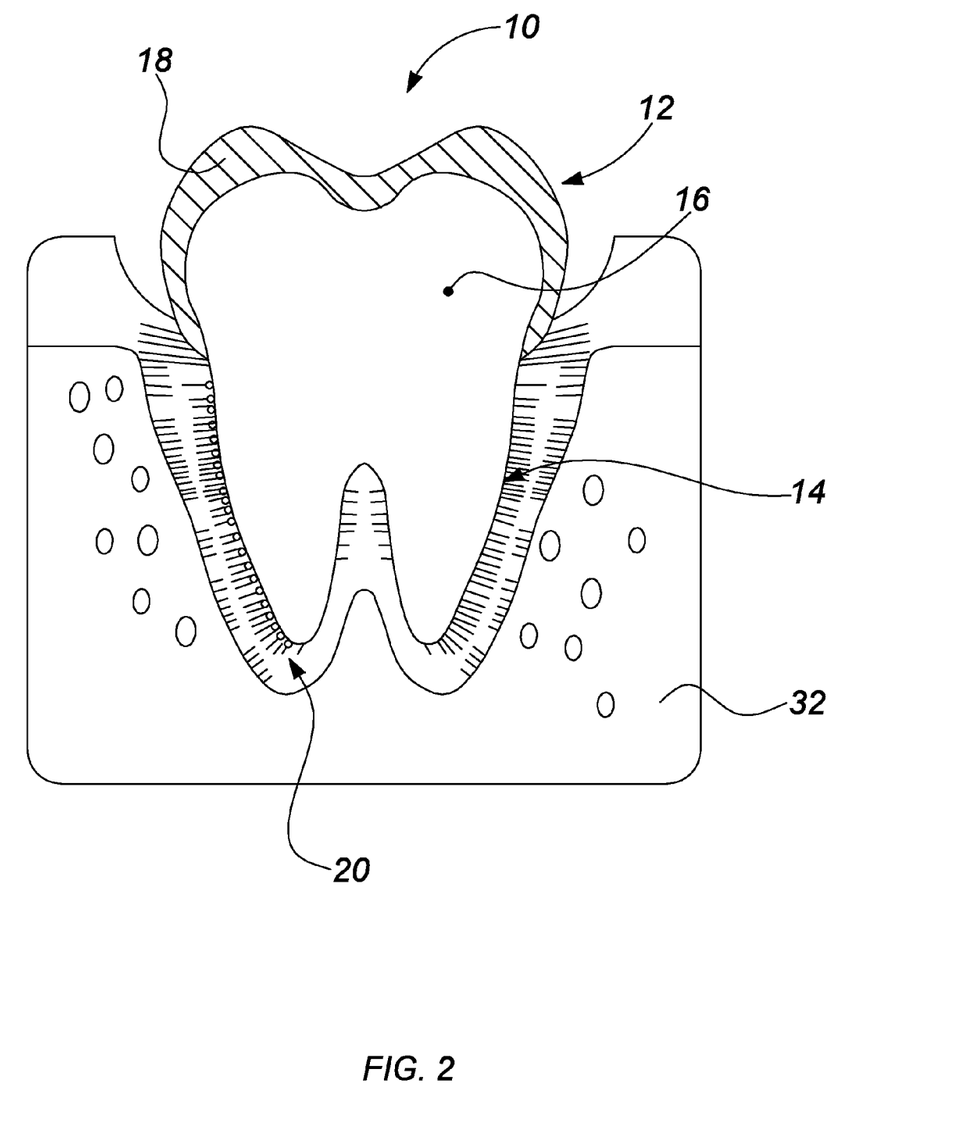
FIG. 2 is a cross sectional view of the tooth implant of FIG. 1 located in the patient's jaw.

Referring to FIGS. 1 and 2, a tooth implant according to a first embodiment of the invention is shown generally at 10 located within a patient's jaw 30. As illustrated, the tooth implant 10 takes the place of and functions in a similar manner to the patent's natural teeth 8. The tooth implant 10 includes a crown portion 12 and a root portion 14. The tooth implant 10 is shaped to correspond to an extracted or missing tooth which it is intended to replace. As illustrated, the tooth implant 10 is formed of a unitary body having the desired shape according to methods which will be described in further detail below.

With reference to FIG. 2, a cross sectional view of the tooth implant within the user's jaw 30 is illustrated. Although the tooth implant 10 is illustrated as being located in the patient's jaw as a lower tooth replacement, it will be appreciated that it may also be utilized as a replacement for any other tooth in the upper or lower jaw. The tooth implant 10 includes an inner core 16, an enamel outer shell 18 over the crown portion 12 and a layer of microscopic protrusions 20 around the root portion 14. As will be more fully described below, the microscopic protrusions enable and encourage growth of periodontal ligaments between the microscopic protrusions and the natural tooth socket so as to replicate the function of a natural tooth. The tooth implant may be formed obtaining an extracted tooth which is to be replaced by the tooth implant 10. Methods of removing or extracting such a tooth from a patient are well known in the art and a model of the tooth may be created from the extracted tooth, the tooth socket or by scans and computer models as are commonly known in the art.

The inner core 16 is formed of any suitable biocompatible materials as are commonly known, such as, by way of non-limiting example, ceramic materials such as zirconia ($ZrO_2$), alumina ($Al_2o_3$) or combinations thereof. The inner core 10 may be formed of any conventional means, such as by way of non-limiting example, moulding, machining, or sintering as are commonly known. In particular, the inner core 10 may be milled from a previously sintered blank of between 20-80% zirconia and 20-80% alumina to a desired shape and thereafter sintered again at a temperature of approximately 2200 to 2900 degrees Fahrenheit (1200 to 1600 degrees Celsius) for a period of between 5-7 hours.

The enamel shell may be formed of any suitable biocompatible material as are commonly known, such as by way of non-limiting example zirconia, alumina, lithium disilicate or combinations thereof with the addition of lower fusing components such as $Na_2O$ or $K_2O$ as is commonly known. The material for forming the outer shell 12 may be sintered to the inner core 10 at a temperature of approximately 200 to 600 degrees Fahrenheit (100 to 300 degrees Celsius) less than the sintering temperature for the inner core for a time period of approximately 1 to 3 hours. The outer shell may have a thickness of between 0.02 and 0.08 inches (0.5 and 2 mm) and may have a color infused therein as desired by a user or may optionally be translucent. It will also be appreciated that the crown portion 12 of the inner core 10 may be formed with dimensions smaller than the tooth to be replaced equivalent to the thickness of the enamel shell 18 at that location such that the finished implant matches the natural tooth which it is intended to replace.

Figure 4A:
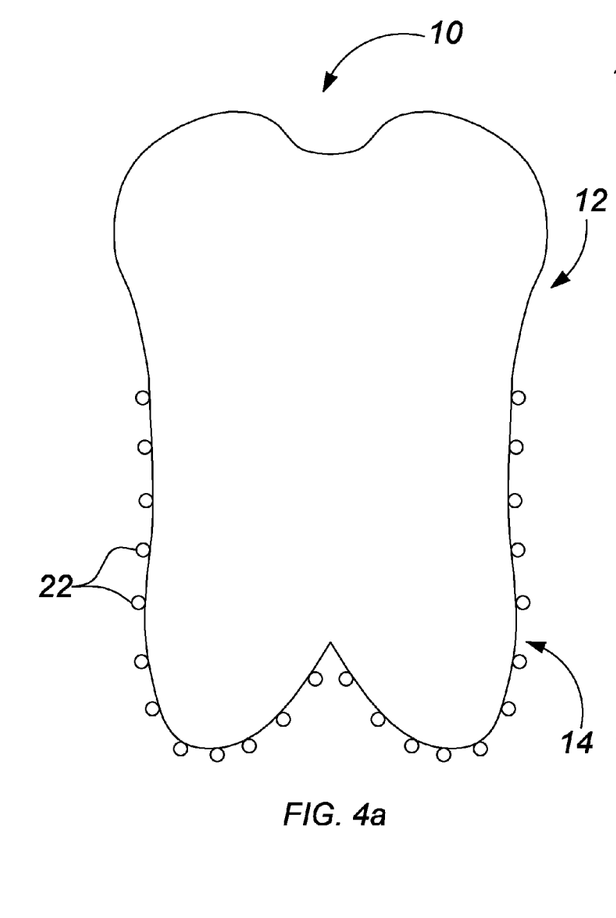
FIG. 4a is a side view of the tooth implant of FIG. 1 with a plurality of particles located on the surface thereof.
Figure 4B:
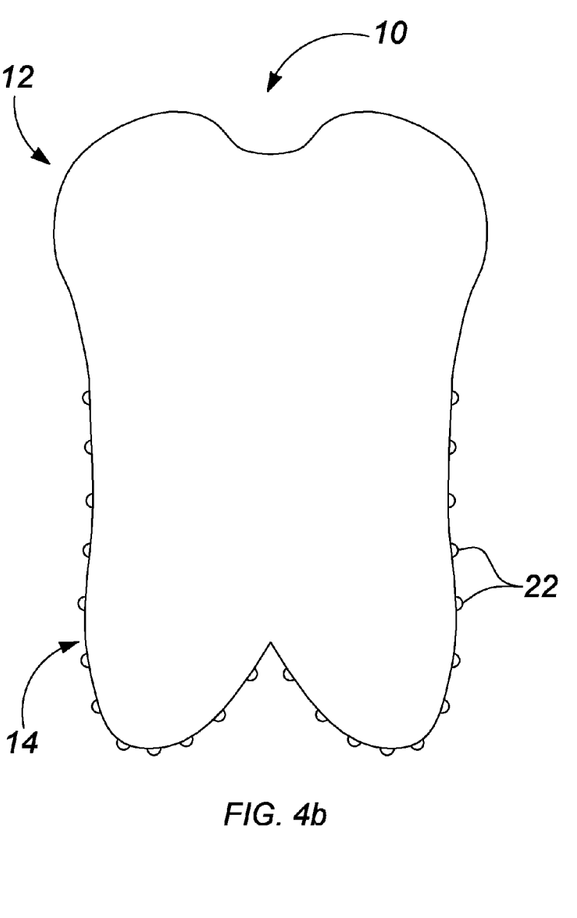
FIG. 4b is a side view of the tooth implant of FIG. 1 with the plurality of particles sintered to the surface thereof.

With reference to FIGS. 4a and 4b, the microscopic protrusions around the tooth implant are formed by adhering a plurality of particles 22 to an outer surface of the root portion 16 as illustrated in FIG. 4b. The particles 22 may formed of biocompatible material as are commonly known, such as by way of non-limiting example zirconia, alumina, lithium disilicate or combinations thereof and may be secured to the outer shell by sintering or other suitable biocompatible methods. The particles 22 are selected to have a sufficiently small enough size, such as, by way of non-limiting example, between 0.002 and 0.008 inches (0.05 and 0.2 mm) and may be sintered to the root portion 18 of the implant as illustrated in FIG. 4b. The particles 22 may also include an addition of $Li_2O$, $Na_2O$ or $K_2O$ in an amount sufficient to lower the required sintering temperature to between 200 to 500 degrees Fahrenheit (100 to 250 degrees Celsius) below the sintering temperature of the inner core. In such a manner, the sintering of the particles 22 to the tooth body will not adversely affect the previously prepared tooth body. Optionally, the particles 22 may be spaced apart by a distance of approximately 0.8 inches (0.2 mm) although other distances may also be utilized. The particles 22 provide a roughness to the tooth implant.

Figure 5:
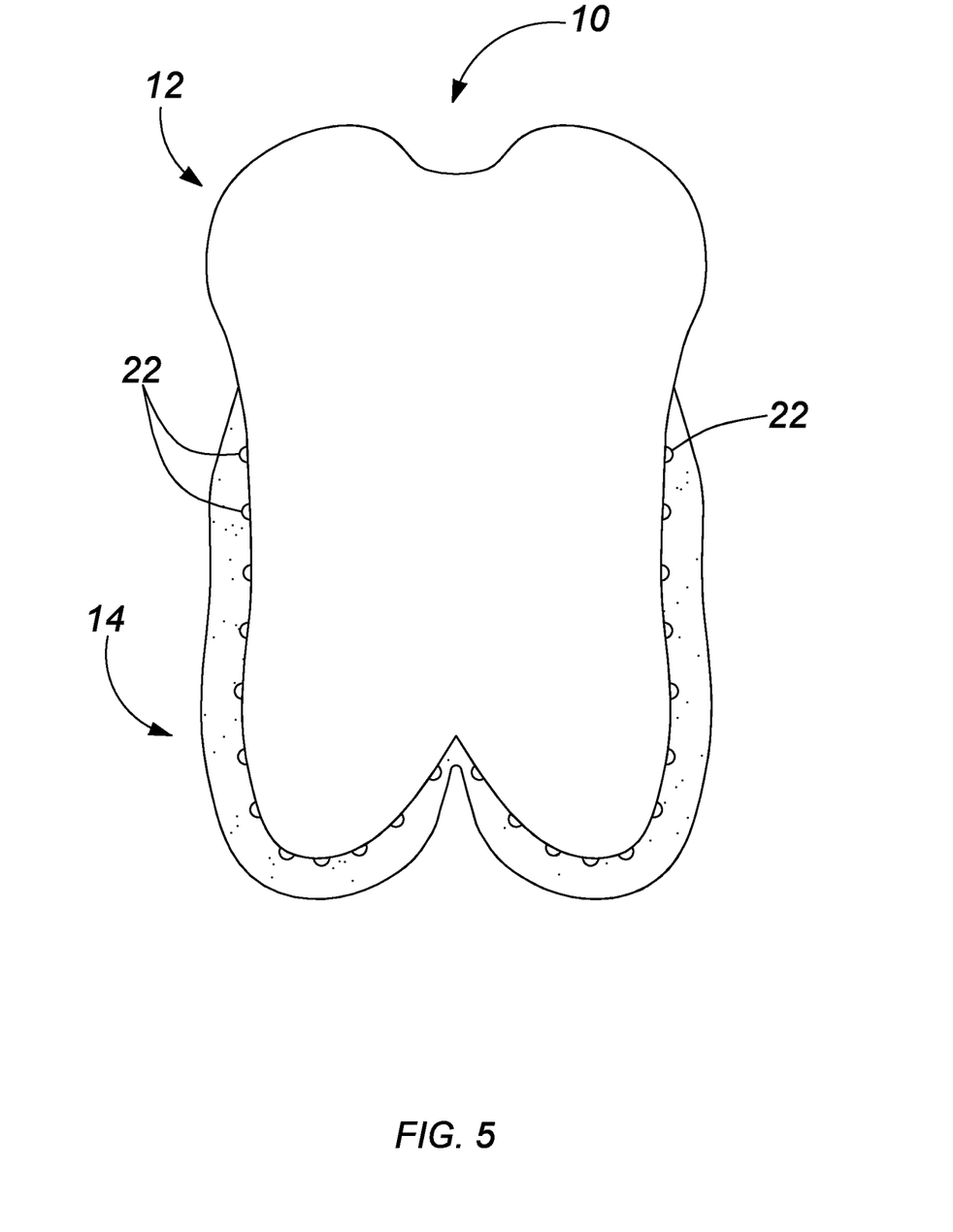
FIG. 5 is a side cross-sectional view of the tooth implant of FIG. 1 with a layer of ceramic powered suspension applied thereto and sintered thereon.

After the seed particles 22 are secured to the outer shell 18, at least the root portion 14 of the tooth implant 10 is has a layer liquefied ceramic suspension 24 applied thereto. The liquefied ceramic suspension is prepared by fusing ceramics, such as, by way of non-limiting example, $ZrO_2$, $Al_2O_3$, $Li_2O$, $Na_2O$, $K_2O$ or combinations thereof with a flux material. The flux material is selected from the group consisting of $Na_2CO_3$, $NaOH$, $K_2CO_3$, $KOH$, $Li_2CO_3$ and $LiOH$ and is mixed with the ceramic in a ration such that the mixture contains between 15-35% ceramic material. It will be appreciated that the flux material assists to lower the melting temperature of the ceramic solution. The mixture of the ceramic material and the fusing material is then fused together and allowed to cool. After the mixture has been cooled, it is milled to a fine powder having particles between 0.0004 and 0.001 inches (0.01 and 0.03 mm). Thereafter the powder may be mixed with water to create an aqueous solution which is applied to the root portion of the tooth body as illustrated in FIG. 5.

Figure 6:
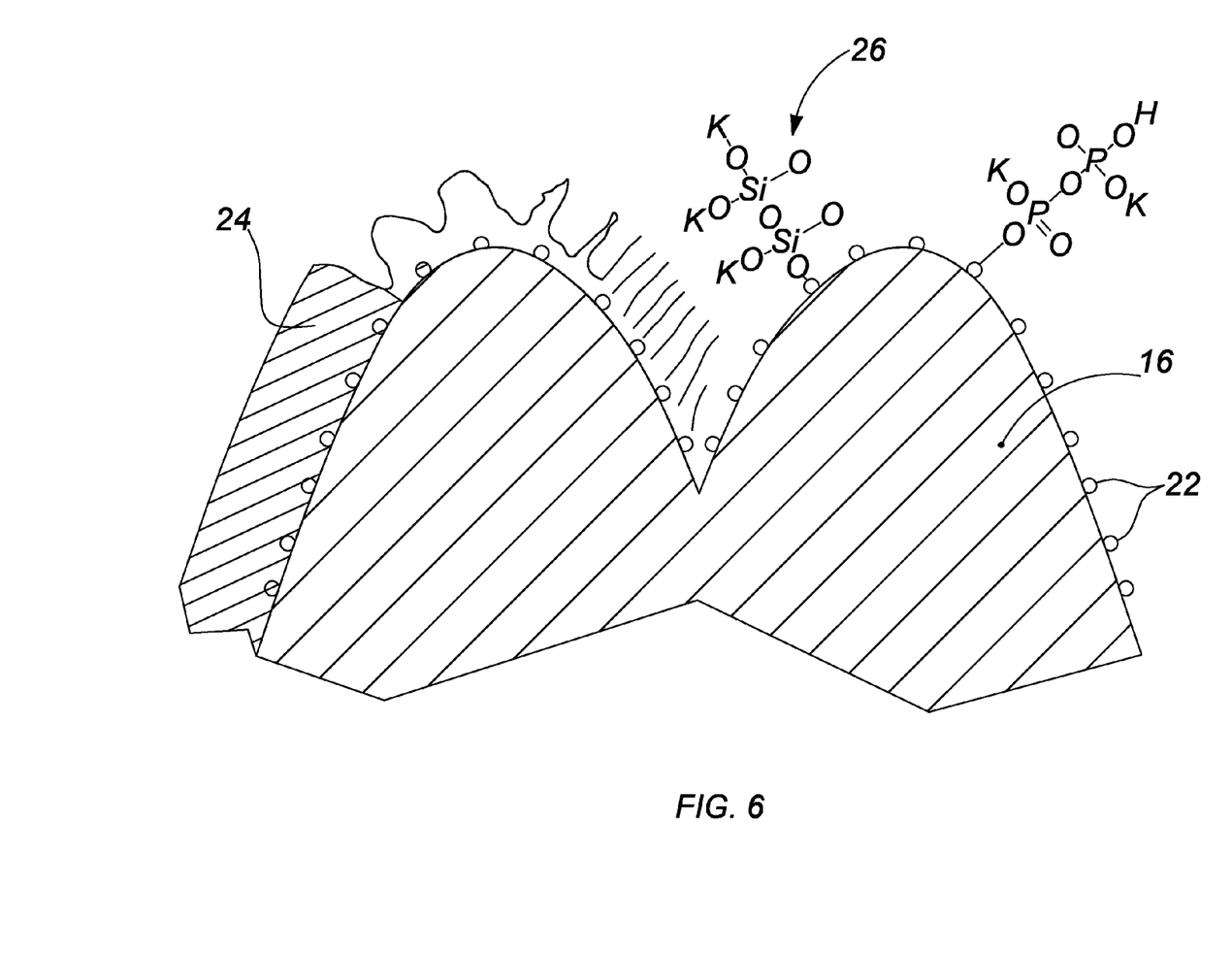
FIG. 6 is a detailed cross sectional view of the tooth implant of FIG. 1 having the ceramic powdered suspension etched by acid after it was sintered.

After the liquefied ceramic suspension is applied to the root portion, the tooth body is heated to a temperature of between 1300 and 1500 degrees Fahrenheit (700 and 800 degrees Celsius) to melt and cure the liquefied ceramic suspension to a glaze on the surface of the root portion. Additionally, after curing a first layer of the liquefied ceramic suspension, further subsequent layers of liquefied ceramic suspension may also be applied to the tooth implant 10 and cured wherein each successive layer of liquefied ceramic suspension will have a lower melting point and be heated to a lower temperature so as to not disturb the layers under. After cooling, the tooth body is exposed to a solution of sulphuric acid H2SO4 to leach the basic oxides out of the melted layer of the liquefied ceramic suspensions thereby leaving acidic oxides, such as, alumina, silica, titania and zirconia in the form of molecular chains 26. Such molecular chains are partially hydrated and positioned to extend from the surface of the root portion. The sulphuric acid solution may be selected to be between 10 and 25% by volume and have a temperature of between 120 and 400 degrees Fahrenheit (50 and 200 degrees Celsius).

Figure 7:
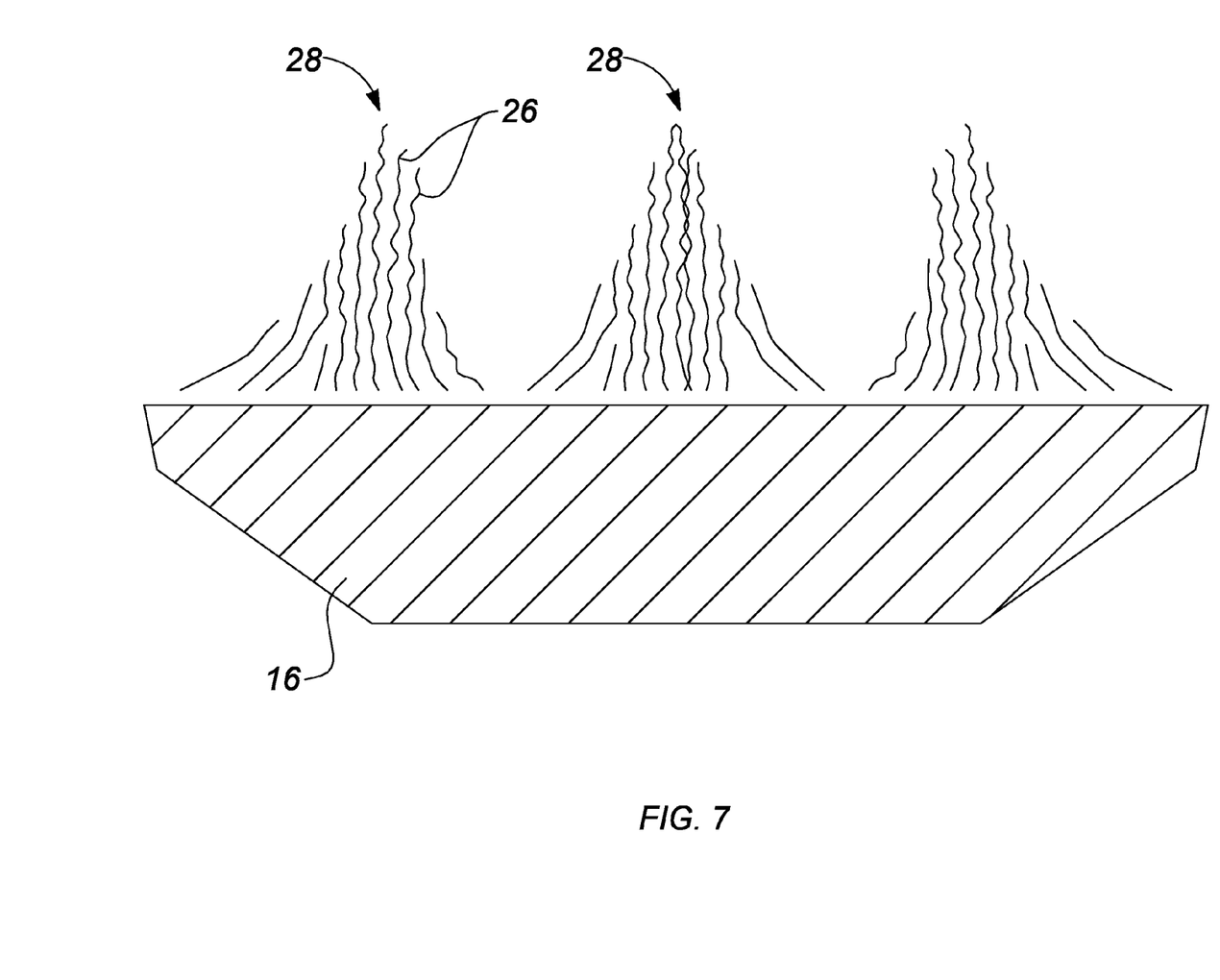
FIG. 7 is a detailed cross sectional view of a plurality of mineral microfibers extending from the tooth implant surface.

After exposure to the sulphuric acid, the tooth body may be exposed to a phosphoric acid solution having a concentration of between 10 and 30% and a temperature of between 1300 and 1500 degrees Fahrenheit (200 and 500 degrees Celsius). The phosphoric acid will further etch the liquefied ceramic suspension layer 24 and expose more molecular chains 26 of the and group them in microfibers 26. The microfibers 28 should have lengths of between 3 and 10 mc and diameters of between 1 and 5 mc with a spacing of between 3 and 5 mc therebetween. After etching the tooth body should be rinsed in a solution of sodium bicarbonate with a concentration of between 1 and 3% by volume to neutralize any remaining acid, rinsed in water and stored in water until ready for use. The above process creates a surface on the root portion 14 of the tooth implant 10 comprising micro and nano mineral fibers consisting of molecular hydrated chains.

Figure 3:
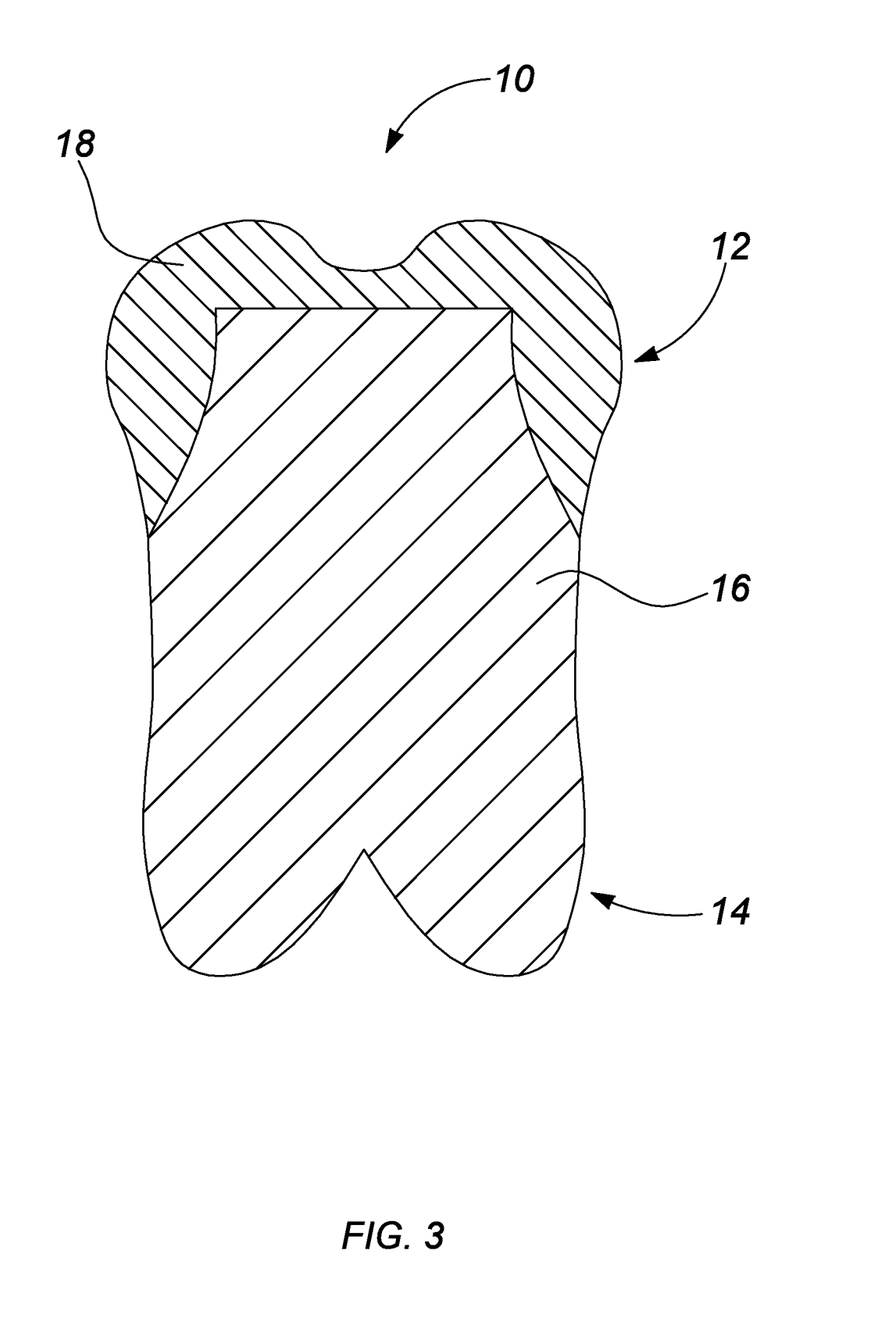
FIG. 3 is a cross sectional view of the tooth implant of FIG. 1 at an intermediate stage of formation.
Figure 8:
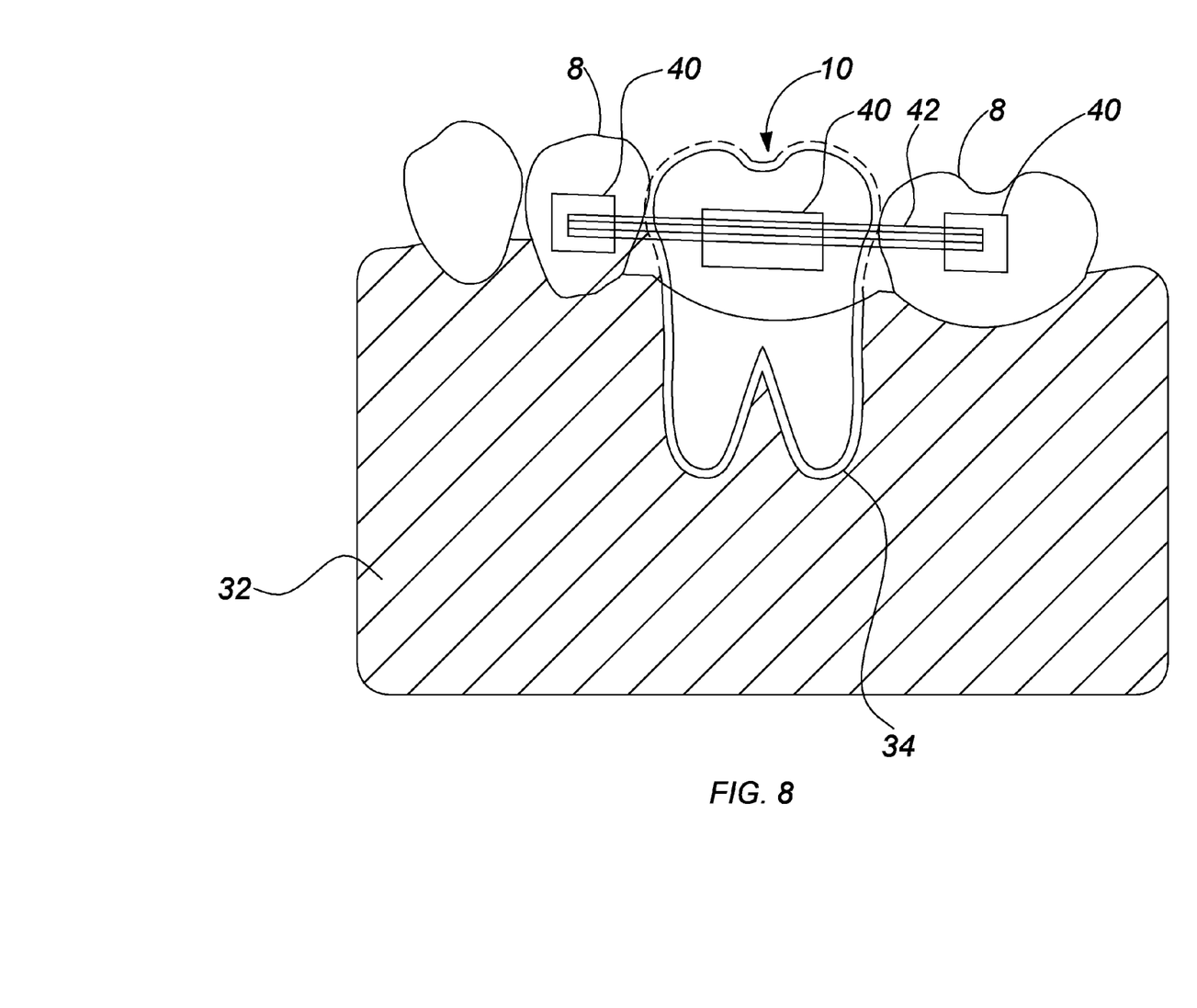
FIG. 8 is a perspective view of the tooth implant of FIG. 1 located in a user's mouth with bracing.

With reference to FIG. 8, a tooth implant 10 according to a first embodiment of the present invention is illustrated in a user's mouth. The tooth implant may be located within the tooth socket 34 left by the extracted tooth which it is to replace and secured to the adjacent teeth 8 with orthodontic brackets 40 and wires 42 or fiberglass splints as are commonly known in the art. The strength of the wires or splints should be selected to limit the degree of movement permitted by the implant while the periodontal membrane is re-establishing. In practice, it has been found that a degree of flexibility of up to 0.02 inches (0.5 mm) has been adequate. Such sprinting permits immediate function loading on the new tooth implant 10 with strictly controlled amplitude of movements to promote the growth of replacement fibrous periodontal-like ligament membranes. As illustrated in FIG. 3, the tooth implant 10 may be sealed within the socket 34 by an adhesive tape 38 to seal the connection between the tooth implant 10 and the socket 34 and to thereby prevent any bacterial invasion. Thereafter the user's socket 34 is encouraged and stimulated to establish a new fibrous periodontal-like ligament membrane 36 by integration of the microfibers 26 and the socket 34 in the user's bone 32 between the root portion 14 of the tooth implant 10 and the socket 34.

While specific embodiments of the invention have been described and illustrated, such embodiments should be considered illustrative of the invention only and not as limiting the invention as construed in accordance with the accompanying claims.

What is claimed is:

1. A method for preparing a dental implant comprising:
   obtaining an model of said tooth to be replaced;
   forming a tooth body corresponding to said model of a sintered ceramic having a first sintering temperature; and
   applying a plurality of particles having a second sintering temperature less than said first sintering temperature to at least a root portion of said tooth body by sintering; and
   forming a layer of microfibers of chains of hydrated minerals to extend from said plurality of particles, wherein said microfibers are formed by:
   applying a layer of liquefied ceramic suspension over said tooth body and plurality of particles;
   heating said dental implant at a temperature less than said second sintering temperature;
   cooling said dental implant;
   exposing said dental implant to a solution of sulfuric acid and
   exposing said dental implant to a solution of phosphoric acid.

2. The method of claim 1 wherein said liquefied ceramic suspension comprises a low fusing ceramic material fused with a layer of a flux material mixed in an aqueous base.

3. The method of claim 2 wherein said ceramic materials are selected from the group consisting of zirconium dioxide, aluminum oxide and lithium silicate.

4. The method of claim 2 wherein said flux material is selected form the group consisting of Na2CO3, NaOH, K2CO3, KOH, Li2CO3 and LiOH.

5. The method of claim 2 wherein said liquid ceramic material and said flux are mixed in a ratio of between 15 and 23% ceramic materials.

6. The method of claim 4 wherein said liquefied ceramic suspension is prepared by fusing said ceramic materials and said flux materials, cooled, milled to a powder and mixed into an aqueous base.

* * * * *